United States Patent
Takano et al.

(10) Patent No.: US 9,404,076 B2
(45) Date of Patent: Aug. 2, 2016

(54) S-ADENOSYL-L-METHIONINE-CONTAINING DRY YEAST COMPOSITION WITH EXCELLENT STORAGE STABILITY AND PROCESS FOR PRODUCING SAME

(75) Inventors: Kentarou Takano, Niigata (JP); Shinyo Gayama, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 13/639,700

(22) PCT Filed: Apr. 5, 2011

(86) PCT No.: PCT/JP2011/058652
§ 371 (c)(1),
(2), (4) Date: Oct. 5, 2012

(87) PCT Pub. No.: WO2011/126030
PCT Pub. Date: Oct. 13, 2011

(65) Prior Publication Data
US 2013/0028878 A1 Jan. 31, 2013

(30) Foreign Application Priority Data
Apr. 7, 2010 (JP) ................................. 2010-088726

(51) Int. Cl.
A23L 1/28 (2006.01)
A61K 36/06 (2006.01)
C12N 1/16 (2006.01)
C12P 19/40 (2006.01)
C12N 1/04 (2006.01)

(52) U.S. Cl.
CPC .. *C12N 1/16* (2013.01); *C12N 1/04* (2013.01); *C12P 19/40* (2013.01)

(58) Field of Classification Search
CPC ............ A23V 2250/315; A61K 36/06; A61K 31/723; A61K 31/736; A61K 31/715; A61K 31/716; A61K 31/738; A23L 1/28; C12N 1/16; C12P 19/40
See application file for complete search history.

(56) References Cited

U.S. PATENT DOCUMENTS

| | | | |
|---|---|---|---|
| 6,207,653 B1 * | 3/2001 | Larm et al. | 514/55 |
| 2003/0039614 A1 * | 2/2003 | Busson et al. | 424/45 |
| 2004/0237663 A1 * | 12/2004 | Farber et al. | 73/861.08 |
| 2006/0188612 A1 * | 8/2006 | Lorenzi | 426/103 |
| 2007/0281009 A1 * | 12/2007 | Kamisono et al. | 424/464 |
| 2008/0102132 A2 * | 5/2008 | Giner et al. | 424/490 |
| 2008/0305192 A1 * | 12/2008 | Brand et al. | 424/756 |
| 2009/0010998 A1 * | 1/2009 | Marchitto et al. | 424/449 |
| 2009/0181001 A1 | 7/2009 | Takano et al. | |
| 2009/0186400 A1 | 7/2009 | Takano et al. | |
| 2010/0075403 A1 | 3/2010 | Takano et al. | |
| 2011/0052623 A1 * | 3/2011 | Ueda et al. | 424/195.16 |

FOREIGN PATENT DOCUMENTS

| | | |
|---|---|---|
| JP | 59 51213 | 3/1984 |
| WO | 2007 129701 | 11/2007 |
| WO | 2007 132831 | 11/2007 |
| WO | 2008 090905 | 7/2008 |
| WO | 2009 024605 | 2/2009 |
| WO | 2009 081833 | 7/2009 |
| WO | 2009 110464 | 9/2009 |

OTHER PUBLICATIONS

'Corn starch—Google translate' is a pdf NPL document of a screenshot of the translation of the term 'corn starch' into Japanese by Google translate.*
NPL pdf document "Guidance memorandum Mar. 4, 2014" accessed Mar. 27, 2014 from http://www.uspto.gov/patents/law/exam/myriad-mayo_guidance.pdf.*
Federal Register, vol. 79, No. 241, Tuesday, Dec. 16, 2014, pp. 74618-74633, accessed from http://www.gpo.gov/fdsys/pkg/FR-2014-12-16/pdf/2014-29414.pdf on Dec. 16, 2014.*
NPL document 'mdc_examples_nature-based_products' accessed from http://www.uspto.gov/patents/law/exam/mdc_examples_nature-based_products.pdf on Dec. 16, 2014.*
Morana, A., et al., "Stabilization of S-adenosyl-L-methionine promoted by trehalose," Biochimica et Biophysica Acta, vol. 1573, pp. 105-108, (2002).
Wang, Y., et al., "Simultaneous quantification of 11 pivotal metabolites in neural tube defects by HPLC-electrospray tandem mass spectrometry," Journal of Chromatography B, vol. 863, pp. 94-100, (2008).
Shiozaki, S., et al., "Production of S-adenosyl-L-methionine by *Saccharomyces sake*," Journal of Biotechnology, vol. 4, pp. 345-354, (1986).
International Search Report Issued Jul. 12, 2011 in PCT/JP11/58652 Filed Apr. 5, 2011.

* cited by examiner

*Primary Examiner* — Ralph Gitomer
*Assistant Examiner* — Trent Clarke
(74) *Attorney, Agent, or Firm* — Oblon, McClelland, Maier & Neustadt, L.L.P.

(57) ABSTRACT

A dry yeast composition which includes 5-adenosyl-L-methionine and a thickener and has excellent storage stability. A thickener is added to a yeast cell concentrate obtained by culturing yeast which has SAMe-producing ability and collecting the cells, and the resultant mixture is dried. Thus, a dry yeast containing a high concentration of 5-adenosyl-L-methionine which has excellent storage stability and excellent bioabsorbability can be easily and profitably produced. It is hence possible to supply a market with a dry yeast composition that contains a high concentration of 5-adenosyl-L-methionine, which is useful as a water-soluble physiologically active substance, and that has excellent storage stability and bioabsorbability.

19 Claims, No Drawings

S-ADENOSYL-L-METHIONINE-CONTAINING DRY YEAST COMPOSITION WITH EXCELLENT STORAGE STABILITY AND PROCESS FOR PRODUCING SAME

This application is a 371 of PCT/JP2011/058652, filed Apr. 5, 2011. Priority to Japanese patent application 2010-088726, filed Apr. 7, 2010, is claimed.

TECHNICAL FIELD

The present invention relates to a dry yeast composition containing a high concentration of S-adenosyl-L-methionine (hereafter referred to as SAMe), which is useful as a water-soluble physiologically active substance, and being excellent in storage stability, and the present invention also relates to a method of producing the dry yeast composition.

BACKGROUND ART

SAMe is a water-soluble physiologically active substance occurring widely in living organisms and playing a key role as a methyl donor involved in the methylation by a wide range of transmethylase in the synthesis and metabolism of nucleic acid, neurotransmitter, phospholipid, hormone, protein, or the like. SAMe is observed in almost all human cells, serves as a cofactor in various biochemical reactions, and is metabolized through three metabolic pathways: transmethylation, transsulfuration, and transaminopropylation. For example, SAMe is an essential substance for the maintenance of cartilage and the biosynthesis of brain chemicals. A recent function study has reported that SAMe has a therapeutic effect on fatty liver, hyperlipemia, arteriosclerosis, insomnia, alcoholic hepatitis, senile dementia, and the like. As just described, SAMe is an important physiologically active substance and is widely used in Euramerican countries as a therapeutic agent for depression, liver disorder, arthritis, and the like or as a health food.

Therefore, it is strongly desired that SAMe be produced and supplied conveniently and inexpensively. Conventionally, the well-known methods of producing SAMe include a fermentation method of using a culture medium containing L-methionine precursor, an enzymatic synthesis method of allowing substrates: adenosine 5'-triphosphate (ATP) and L-methionine to interact with SAMe synthase (methionine adenosyltransferase) isolated and purified from microorganisms, such as yeast, and a chemical synthesis method.

The enzymatic synthesis method, in which SAMe is enzymatically synthesized by allowing substrates: adenosine 5'-triphosphate (ATP) and L-methionine to interact with SAMe synthase (methionine adenosyltransferase) isolated and purified from microorganisms, such as yeast, has the advantage that SAMe is accumulated in large quantities and not required to be extracted from yeast cells, as compared with the fermentation method. However, this method has various problems including the complex preparation of enzymes, the low activity of obtained enzymes, the necessity of removing interfering substances, such as ATPase, and the extremely high cost of ATP as a substrate, and therefore cannot necessarily be a practical method. In addition, the recent progress of genetic engineering has led these enzymes to be prepared more conveniently by using cloned SAMe synthase genes so as to solve the problems involved in the preparation of enzymes. However, high-cost ATP still needs to be used as a substrate, and other practical problems have not been solved.

Furthermore, SAMe is thermolabile and easily degradable even at normal temperature, this presenting a major obstacle to its application to a medicine and a health food. To eliminate this problem, numerous attempts have been made to improve the storage stability. For example, a method is commonly used in which SAMe composition obtained by the above-mentioned production method is purified through chromatography or the like, and then converted into a salt of sulfuric acid, p-toluenesulfonic acid, or butanedisulfonic acid to stabilize SAMe (see Patent Document 1), or in which the purified SAMe is added with an additive to give a stabilized SAMe composition (for example, see also Patent Document 1). These methods require great time and expense and therefore have great difficulty in producing and providing important SAMe inexpensively as a therapeutic agent and a health food. Recently, studies have been made on SAMe-containing dry microorganisms by using orally available microorganisms having an ability to produce SAMe more conveniently and more inexpensively with fewer steps of purification (for example, see Patent Document 2 and Non-Patent Document 2). At the present time, however, SAMe-containing dry microorganisms involves a problem of lower storage stability than purified SAMe and SAMe compositions.

PRIOR ART

Patent Documents

Patent Document 1: JP 59-51213A
Patent Document 2: WO 2008/090905

Non-Patent Documents

Non-Patent Document 1: Biochemica et Biophysica Acta, 1573, 105-108, (2002)
Non-Patent Document 2: J of Chromatography B, 863, 94-100 (2008)

DISCLOSURE OF THE INVENTION

An objective of the present invention is to establish a convenient and inexpensive process to produce a dry yeast composition containing a high concentration of SAMe and exhibiting excellent storage stability.

To solve the above-mentioned problems, the inventors made a great effort to study the method of economically producing a composition containing a high concentration of SAMe and exhibiting excellent performance in long preservation under stable condition. Then, the inventors have found that a dry yeast composition containing a high concentration of the intended SAMe and having excellent storage stability can be conveniently produced in good yield by producing and accumulating a high concentration of SAMe in yeast cells using orally available SAMe-producing yeast; separating the yeast cells from the culture solution by separation means, such as centrifugation; adding a thickener to the obtained yeast cell concentrate; and then drying the resultant mixture. As a result of this finding, the inventors have achieved the present invention. The present inventors also have found that the SAMe-containing dry yeast composition of the invention has excellent bioabsorbability in addition to storage stability. As a result of this finding, the inventors have achieved the present invention.

The present invention provides:
(1) an S-adenosyl-L-methionine-containing dry yeast composition comprising S-adenosyl-L-methionine and a thickener, and (2) a method of producing an S-adenosyl-L-methionine-containing dry yeast composition, the method comprising using an S-adenosyl-L-methionine-producing yeast, adding a thickener to a yeast cell concentrate obtained from a culture solution of the yeast cell, and drying the resultant mixture.

EFFECTS OF THE INVENTION

The S-adenosyl-L-methionine-containing dry yeast composition of the invention has excellent storage stability and excellent bioabsorbability. Therefore, the dry yeast composition is applicable to a medicine and a health food by crushing the dry yeast composition into powder; by adding another physiological component or another additive, such as an excipient, to the powdery dry yeast composition if necessary and then compressing and tabletting the resultant mixture into a tablet composition; by granulating the powdery dry yeast composition into granule; by encapsulating the granulated dry yeast composition, or the like. Thus, the invention provides a useful composition as a water-soluble physiologically active substance for a medicine and a health food.

Furthermore, the present invention provides a convenient and inexpensive method of producing a composition containing a high concentration of S-adenosyl-L-methionine and having excellent storage stability and furthermore a convenient and inexpensive method of producing SAMe-containing dry yeast composition having excellent bioabsorbability.

MODE FOR CARRYING OUT THE INVENTION

The type of yeast used in the present invention is not limited as long as the yeast is orally available and has SAMe-producing ability, and includes, for example, yeast belonging to genus *Saccharomyces*, with *Saccharomyces cerevisiae* being more preferable. The dry yeast is widely used as a health food and the like, because the dry yeast contains a high proportion of useful components, such as 5'-nucleotide, free amino acid, glutathione with antioxidative effect helpful for improving liver function, and β-glucan and dietary fiber with the effect of improving immunity and regulating the function of intestine.

The carbon source to be used for culturing the yeast mentioned above is not particularly limited as long as anabolized by the yeast. Examples of the carbon source include glucose, saccharose, starch, carbohydrate, such as blackstrap molasses, alcohol, such as ethanol, and organic acid, such as acetic acid. The nitrogen source is also not limited as long as anabolized by the yeast to be used. Examples of the nitrogen source include an inorganic nitrogen-containing compound, such as ammonia, nitric acid, and urea and a substance containing an organic nitrogen-containing compound, such as yeast extract and malt extract. As an inorganic salt, a salt of phosphoric acid or a salt of potassium, sodium, magnesium, calcium, iron, zinc, manganese, cobalt, copper, or molybdenum is used. Furthermore, methionine, adenine, and adenosyl ribonucleoside that form the skeletal framework of SAMe can be added for culture.

As a medium, the L-methionine-containing medium (Shiozaki S. et al., J. Biotechnology, 4, 345-354 (1986)) was used.

The yeast is inoculated onto a medium containing medium components, such as sucrose, yeast extract, L-methionine, urea, glycine, potassium dihydrogenphosphate, magnesium sulfate heptahydrate, biotin, calcium chloride dihydrate, and trace metallic salt. The inoculated yeast is aerobically cultured while carbon sources, such as sucrose and/or ethanol, are fed into the inoculated medium, to obtain SAMe-containing yeast cells.

The culture temperature may be 20 to 35° C. and the pH of the culture solution may be pH 4 to 7, although depending upon the type of yeast to be used.

In order to increase the SAMe content in the yeast cells, the yeast is preferably cultured aerobically. The type of culture tank is not limited as long as it can be ventilated and stirred if necessary and, for example, a mechanical stirring culture tank, an air-lift culture tank, a bubble column culture tank, and the like are usable.

The medium ingredients, such as carbon source, nitrogen source, various inorganic salts, various additives, and the like, are continuously or intermittently supplied together or individually. For example, the substrate, such as saccharose and ethanol, may be supplied to the fermenter as a mixture with other medium ingredients, or may be supplied to the fermenter independently from other medium ingredients. The pH of the culture solution is controlled by an acid or alkali solution. Examples of the alkali include ammonia and urea which are also used as the nitrogen source and non-nitrogen base, such as sodium hydroxide and potassium hydroxide. Examples of the acid include an inorganic acid, such as phosphoric acid, sulfuric acid, and nitric acid, and an organic acid. The pH of the culture solution can be controlled also by using an inorganic salt, such as salt of phosphoric acid, potassium salt, sodium salt, and salt of nitric acid.

The culture is carried out under the conditions described above. The culture solution is withdrawn from the culture tank when a desired amount of SAMe is accumulated in the yeast cells and then the yeast cells are separated. The separation method is not limited as long as the yeast cells can be efficiently separated and cleaned, with a counterflow yeast separator or an ultrafiltration system utilizing a separation membrane being preferred.

Then, the thickener is added to the separated yeast cell concentrate. This increases the storage stability and the bioabsorbability of SAMe in the dry yeast, improves the yield in the drying process of the yeast, and masks odor peculiar to the dry yeast. The amount of a thickener to be added based on the S-adenosyl-L-methionine containing dry yeast composition is preferably 0.1 to 70% by mass, more preferably 0.4 to 70% by mass, still more preferably 0.7 to 70% by mass, and particularly preferably 4.5 to 70% by mass. The amount less than 0.1% by mass results in insufficient storage stability of SAMe in the dry yeast. The amount more than 70% by mass produces no additional effect and the storage stability of SAMe tends to decrease depending upon the amount of use.

The thickener referred to in the present invention includes various thickeners, such as gelling agents, which increase the viscosity and can be added to foods.

Examples of the thickener usable in the invention includes:

(1) a thickener derived from microbiological sources, such as xanthan gum, gellan gum, curdlan, algin xanthan gum, pullulan, and natto gum;

(2) a thickener derived from seeds, such as guar gum, tara gum, locust bean gum, tamarind gum, and psyllium seed gum;

(3) a thickener derived from plants, such as cellulose, methylcellulose, hydroxypropylcellulose, hydroxypropylmethylcellulose, carboxymethylcellulose, starch, and sodium carboxymethylate;

(4) a thickener derived from seaweeds, such as carrageenan, sodium alginate, alginic acid, and propylene glycol ester of alginic acid;

(5) a thickener derived from resin, such as gum arabic, tragacanth gum, shellac, and arabinogalactan;
(6) a thickener derived from crustaceans, such as chitosan and chitin; and
(7) a thickener, such as pectin, mannan, hyaluronic acid, chondroitin, agar-agar, collagen, albumin, zein, casein, and sodium caseinate. At least one thickener selected from those mentioned above is used.

More preferred are:
(1) a thickener derived from microbiological sources, such as xanthan gum, gellan gum, curdlan, algin xanthan gum, pullulan, and natto gum;
(2) a thickener derived from seeds, such as guar gum, tara gum, locust bean gum, tamarind gum, and psyllium seed gum;
(5) a thickener derived from resin, such as gum arabic, tragacanth gum, shellac, and arabinogalactan;
(6) a thickener derived from crustaceans, such as chitosan and chitin; and
(7) a thickener, such as pectin, mannan, hyaluronic acid, chondroitin, agar-agar, collagen, albumin, zein, casein, and sodium caseinate.

Particularly preferred are:
(1) a thickener derived from microbiological sources, such as xanthan gum, gellan gum, curdlan, algin xanthan gum, pullulan, and natto gum; and
(2) a thickener derived from seeds, such as guar gum, tara gum, locust bean gum, tamarind gum, and psyllium seed gum.

The thickener used in the present invention is used widely for foods, cosmetics, and medicines, so that it can be safely applied.

After a thickener is added in this way, water is evaporated from the yeast cell concentrate by spray drying with a spray dryer, freeze drying, or the like to produce a SAMe-containing dry yeast composition.

The spray drying is preferably carried out at an inlet temperature of 210° C. or less and an exit temperature of 110° C. or less. The freeze drying is preferably carried out at a final shell temperature of 30° C. or less. The SAMe-containing composition of the present invention preferably has a water content of 5.0% by mass or less from the viewpoint of storage stability.

The dry yeast composition may be crushed into powder. After another physiological component or another additive, such as an excipient, is added to the powdery dry yeast, if needed, the resultant mixture of the dry yeast may be compressed and tabletted into a tablet composition. In addition, the surface of the tablet composition may be coated.

Alternatively, the powdery dry yeast composition may be granulated, or the powdered or granulated dry yeast composition may be encapsulated.

EXAMPLES

The present invention will be explained below in more detail with reference to examples and comparative examples. However, it should be noted that the scope of the invention is not limited thereto.

Examples 1 to 4

(a) Culture of Yeast Cells

According to the above-mentioned well-known culture method, *Saccharomyces cerevisiae* IFO2346 belonging to genus *Saccharomyces* was inoculated onto an L-methionine-containing medium (Shiozaki S., et al., J. Biotechnology, 4, 345-354 (1986)). The inoculated yeast was aerobically cultured for six days at a culture temperature of 27 to 29° C. under stirring while introducing air, to obtain 18 L of a yeast culture solution with a yeast cell concentration of 3.5 wt % and an SAMe content of 205 mg/g of dry yeast.

(b) Collection of Yeast Cells

The obtained 18 L of yeast culture solution was centrifuged by a continuous rotary type centrifuge (Hitachi Himac Centrifuge CR10B2) to obtain 3.4 kg of a liquid yeast cell concentrate with a yeast concentration of 18% by mass on dry basis.

(c) Addition of Thickener to Yeast Cell Concentrate

To the obtained 3.4 kg of yeast cell concentrate, xanthan gum was added in an amount of 0.02, 0.2, 2.2, or 11.1 times by mass of SAMe in the yeast concentrate. The mixture was stirred at a room temperature for 30 min to obtain a yeast cell concentrate added with xanthan gum.

(d) Production of Dry Yeast

The yeast cell concentrate added with xanthan gum was poured into a stainless tray of a freeze dryer (available from ULVAC, Inc.), frozen at −50° C., and then freeze-dried for 36 h at a final shelf temperature of 25° C. The obtained freeze-dried yeast was crushed into powdery dry yeast. The powdery dry yeast thus obtained was packed in a glass container, which was then sealed. Then, a storage stability test was carried out under accelerated condition of 40° C. and 75% RH. The result of the accelerated storage stability test at 40° C. and 75% RH are shown in Table 1. The SAMe residual rate was determined by a comparative determination using liquid chromatography on SAMe extracted from the SAMe-containing dry yeast by a well-known method using perchloric acid. The presence of odor after storage was organoleptically determined by five panelists. If all of the five panelists felt no odor, the result was rated as "A," if one or two of the five panelists felt odor, the result was rated as "B," and if three or more of the five panelists felt odor, the result was rated as "C."

The SAMe measurement by liquid chromatography in the present invention was made under the following conditions.
Analysis Conditions Used
Column: Cosmosil 4.6φ×100 mm available from Nacalai Tesque, Inc.
Eluant: 0.2 M $KH_2PO_4$ aqueous solution/methanol=95/5
Flow rate: 0.7 mL/min
Detector: UV (260 nm)
SAMe retention time: about 150 s Examples 5 to 8

A powdery dry yeast was obtained in the same manner as in Example 1 except for adding curdlan to the yeast cell concentrate. The SAMe content of the powdery dry yeast, the mass of the additive, the result of the storage stability test for the powdery dry yeast packed in a sealed glass container under accelerated conditions of 40° C. and 75% RH, and the result of the organoleptic test are shown in Table 1.

Example 9

A powdery dry yeast was obtained in the same manner as in Example 1 except for adding guar gum to the yeast cell concentrate in an amount of 0.2 time by mass of SAMe in the yeast cell concentrate. The SAMe content of the powdery dry yeast, the mass of the additive, the result of the storage stability test for the powdery dry yeast packed in a sealed glass container under accelerated conditions of 40° C. and 75% RH, and the result of the organoleptic test are shown in Table 1.

Example 10

A powdery dry yeast was obtained in the same manner as in Example 1 except for adding tamarind gum to the yeast cell concentrate in an amount of 0.2 time by mass of SAMe in the yeast cell concentrate. The SAMe content of the powdery dry yeast, the mass of the additive, the result of the storage stability test for the powdery dry yeast packed in a sealed glass container under accelerated conditions of 40° C. and 75% RH, and the result of the organoleptic test are shown in Table 1.

Example 11

A powdery dry yeast was obtained in the same manner as in Example 1 except for adding gellan gum to the yeast cell concentrate in an amount of 0.2 time by mass of SAMe in the yeast cell concentrate. The SAMe content of the powdery dry yeast, the mass of the additive, the result of the storage stability test for the powdery dry yeast packed in a sealed glass container under accelerated conditions of 40° C. and 75% RH, and the result of the organoleptic test are shown in Table 1.

Comparative Example 1

A powdery dry yeast was obtained in the same manner as in Example 1 except for omitting the addition of xanthan gum to the yeast cell concentrate.

The SAMe content of the powdery dry yeast, the mass of the additive, the result of the storage stability test for the powdery dry yeast packed in a sealed glass container under accelerated conditions of 40° C. and 75% RH, and the result of the organoleptic test are shown in Table 1.

Comparative Example 2

A powdery dry yeast was obtained in the same manner as in Example 1 except for adding trehalose to the yeast cell concentrate in an amount of 2.2 times by mass of SAMe in the yeast cell concentrate. The SAMe content of the powdery dry yeast, the mass of the additive, the result of the storage stability test for the powdery dry yeast packed in a sealed glass container under accelerated conditions of 40° C. and 75% RH, and the result of the organoleptic test are shown in Table 1.

TABLE 1

| Examples | Additive | Mass of additive to dry yeast composition (%) | Additive amount to solution before drying (% by mass) | SAMe content in dry yeast at start of test (% by mass) |
|---|---|---|---|---|
| Comparative Example 1 | none | 0.0 | 0.0 | 14.5% |
| Example 1 | xanthan gum | 0.48 | 0.1 | 16.1% |
| Example 2 | xanthan gum | 4.6 | 1.0 | 12.3% |
| Example 3 | xanthan gum | 32.0 | 10.0 | 11.9% |
| Example 4 | xanthan gum | 68.6 | 50.0 | 5.2% |
| Example 5 | curdlan | 0.48 | 0.1 | 15.9% |
| Example 6 | curdlan | 4.6 | 1.0 | 13.3% |
| Example 7 | curdlan | 32.0 | 10.0 | 11.6% |
| Example 8 | curdlan | 68.6 | 50.0 | 5.1% |
| Example 9 | guar gum | 4.6 | 1.0 | 9.1% |
| Example 10 | tamarind gum | 4.6 | 1.0 | 14.6% |
| Example 11 | gellan gum | 4.6 | 1.0 | 12.2% |
| Comparative Example 2 | trehalose | 32.0 | 10.0 | 12.5% |

| Example | Storage stability test SAMe residual rate (%) After 30 days | After 45 days | After 60 days | Presence of odor after 60 days* |
|---|---|---|---|---|
| Comparative Example 1 | 5.8% | 0.0% | 0.0% | C |
| Example 1 | 60.1% | 46.4% | 28.1% | B |
| Example 2 | 99.6% | 99.6% | 99.5% | A |
| Example 3 | 99.7% | 99.7% | 99.7% | A |
| Example 4 | 99.8% | 99.8% | 99.7% | A |
| Example 5 | 58.8% | 44.5% | 25.1% | B |
| Example 6 | 94.9% | 94.7% | 94.4% | A |
| Example 7 | 99.8% | 99.8% | 99.7% | A |
| Example 8 | 99.8% | 99.8% | 99.8% | A |
| Example 9 | 99.7% | 99.7% | 99.6% | A |
| Example 10 | 92.8% | 92.5% | 92.3% | A |
| Example 11 | 99.7% | 99.6% | 99.5% | A |
| Comparative Example 2 | 10.4% | 0.0% | 0.0% | C |

*Organoleptic test: C: strong offensive odor, B: slight offensive odor, and A: no odor

Examples 12 to 19

An SAMe-containing yeast concentrate having a solid concentration of 18.2% by mass (SAMe content: 3.7% by mass) was obtained by using a 200-L culture tank. To the obtained concentrate, each of additives: x-carrageenan (Example 12), xanthan gum (Example 13), guar gum (Example 14), tamarind gum (Example 15), curdlan (Example 16), gellan gum (Example 17), alginic acid (Example 18), and Ceolus ST-02 (crystalline cellulose) (Example 19), was added in an amount of 1% by mass. Then, the recovery and the SAMe content (% by mass) after freeze-drying, and the residual rates of SAMe after 30- and 60-day storage at 40° C. were determined.

The conditions employed in Examples 12 to 19 are described below.

(a) Culture of Yeast cell

Culture was carried out in the same conditions as in Example 1 to obtain 120 L of a yeast culture solution with a yeast cell concentration of 3.5% by mass and an SAMe content of 201.5 mg/g of dry yeast.

(b) Collection of Yeast Cells

The obtained 120 L of yeast culture solution was centrifuged by a continuous rotary type centrifuge (Hitachi Himac Centrifuge CR10B2) to obtain 23.4 kg of a liquid yeast cell concentrate with a yeast concentration of 18% by mass on dry basis.

(c) Addition of Thickener to Yeast Cell Concentrate

To the obtained 23.4 kg of yeast cell concentrate, each of thickeners of Examples 12 to 19 was added in an amount of 10 time by mass of SAMe in the yeast concentrate. The mixture was stirred at a room temperature for 30 min to obtain each yeast cell concentrate added with each of thickeners of Examples 12 to 19.

(d) Production of Dry Yeast

Each of the yeast cell concentrates in which the respective thickeners of Examples 12 to 19 were added was poured into a stainless tray of a freeze dryer (available from ULVAC, Inc.), frozen at −50° C., and then freeze-dried for 36 h at a final shelf temperature of 25° C. The obtained freeze-dried yeast was crushed into powdery dry yeast. The powdery dry yeast thus obtained was packed in a glass container, which was then sealed. Then, a storage stability test was carried out under accelerated condition of 40° C. and 75% RH. The result of the accelerated storage stability test at 40° C. and 75% RH are shown in Table 2. The SAMe residual rate was determined by the method described above. The mixing state of the additive and the SAMe-containing yeast concentrate was evaluated by visually observing the dispersion state. The mixing state of the additive, the recovery and the form of yeast cells and the SAMe content (% by mass) after freeze-drying, and the residual rates of SAMe after 30- and 60-day storage at 40° C. are shown in Table 2.

TABLE 2

| | Additive | Additive amount to concentrate before drying (% by mass) | Mixing state of additive* | Recovery after drying |
|---|---|---|---|---|
| Comparative Example 1 | none | 0% | — | 97% |
| Example 12 | κ-carrageenan | 1% | A | 97% |
| Example 13 | xanthan gum | 1% | B | 98% |
| Example 14 | guar gum | 1% | A | 98% |
| Example 15 | tamarind gum | 1% | A | 97% |
| Example 16 | curdlan | 1% | B | 96% |
| Example 17 | gellan gum | 1% | B | 96% |
| Example 18 | alginic acid | 1% | B | 98% |
| Example 19 | Ceolus ST-02 (crystalline cellulose) | 1% | A | 98% |

| | Form after drying | SAMe content after drying (% by mass) | Storage stability test Residual rate (%) | |
|---|---|---|---|---|
| | | | After 30 days | After 60 days |
| Comparative Example 1 | powder | 14.4% | 6.0% | 0.0% |
| Example 12 | powder | 14.0% | 70.1% | 58.5% |
| Example 13 | powder | 12.3% | 99.5% | 99.3% |
| Example 14 | powder | 9.1% | 99.6% | 99.5% |
| Example 15 | powder | 14.6% | 93.1% | 92.2% |
| Example 16 | gum | 13.3% | 95.0% | 94.1% |
| Example 17 | gum | 12.2% | 99.6% | 99.4% |
| Example 18 | powder | 16.1% | 69.5% | 54.0% |
| Example 19 | powder | 16.8% | 76.8% | 64.0% |

*Organoleptic test: A: uniformly dispersed, B: nearly uniformly dispersed

Comparative Example 3

A powdery dry yeast was obtained in the same manner as in Example 1 except for carrying out the culture in a medium not containing L-methionine SAMe was not contained in the obtained powdery dry yeast. The following experimentation was carried out by using the obtained powder dry yeast.

Performance Tests 1 to 5 and Comparative Performance Evaluations 1 and 2

The dry yeasts obtained in Examples 2, 6, 9, 10, and 11 and Comparative Examples 1 and 3 were tested for the bioabsorbability as Performance Test Examples 1 to 5 and Comparative Performance Evaluations 1 and 2 by using SD rats (eight-week-old male rats, number of rats n=3 for each group) in the same manner as described in Non-Patent Document 2.

The bioabsorbability tests were carried out in accordance with the method described in Non-Patent Document 2 (J of Chromatography B, 863, 94-100 (2008)). The dry yeast was dispersed in distilled water and orally administered to the rats in a dose of 300 mg/kg of rat on the basis of SAMe. Blood was taken from the rats 0.5, 2, 3 and 5 h after the oral administration and then promptly centrifuged to separate plasma components. Then, SAMe component extract obtained by using perchloric acid was analyzed by LC-MS-MS (Liquid chromatography coupled with mass spectrometry) method using a high speed liquid chromatograph (HPLC) under the following condition. The concentration of SAMe in plasma was highest two hours after the oral administration of each dry yeast. The result of the bioabsorbability test two hours after the oral administration of each dry yeast is shown in Table 3. The results of Table 3 show that the bioabsorbability of each Test Example wherein the dry yeast added with a thickener was used was more improved than that of Evaluation 1 wherein the dry yeast of Comparative Example 1 added with no thickener was used.

The analyzer and the conditions used in the bioabsorbability tests are as follows.

LC-MS-MS Method
  LC-MS-MS system: Accela, LTQ orbitrap Discovery available from Thermo Fisher Scientific, Inc.
HPLC Condition
  Column: Intersil ODS-3 (4.6 mm×150 mm) available from GL Sciences, Inc.
  Flow rate: 0.5 mL/min
  Column oven: 40° C.
  Detector: UV (260 nm)
  SAMe retention time: about 145 s
  Injection rate: 10 μl
  Eluant: 2 mmol/L aqueous solution of heptafluorobutyric acid:acetonitrile=30:70
MS Condition
  Ion Source: ESI
  Ion Polarity Mode: positive
  Scan Mode Type: FT full mass
  Resolution: 30000
  Mass Range: m/z 360-410

TABLE 3

| | Dry yeast | Additive | Additive amount to dry yeast composition before drying (% by mass) |
|---|---|---|---|
| Evaluation 1 | Comparative example 1 | none | 0.0 |
| Evaluation 2 | Comparative example 3 | none | 0.0 |
| Test Example 1 | Example 2 | xanthan gum | 4.6 |
| Test Example 2 | Example 6 | curdlan | 4.6 |
| Test Example 3 | Example 9 | guar gum | 4.6 |
| Test Example 4 | Example 10 | tamarind gum | 4.6 |
| Test Example 5 | Example 11 | gellan gum | 4.6 |

TABLE 3-continued

|  | Additive amount to solution before drying (% by mass) | SAMe content in dry yeast at start of test (% by mass) | Concentration of SAMe in plasma two hours after oral administration (μg/ml) |
|---|---|---|---|
| Evaluation 1 | 0.0 | 14.5% | 0.96 |
| Evaluation 2 | 0.0 | 0.0% | 0.13 |
| Test Example 1 | 1.0 | 12.3% | 1.33 |
| Test Example 2 | 1.0 | 13.3% | 1.21 |
| Test Example 3 | 1.0 | 9.1% | 1.83 |
| Test Example 4 | 1.0 | 14.6% | 1.18 |
| Test Example 5 | 1.0 | 12.2% | 1.19 |

INDUSTRIAL APPLICABILITY

The composition containing S-adenosyl-L-methionine and having excellent storage stability and the composition having excellent bioabsorbability are effectively used as a physiologically active substance for medicines and health foods.

The production method of the present invention is useful as a method of conveniently and inexpensively producing a composition containing a high concentration of S-adenosyl-L-methionine and having excellent storage stability.

What is claimed is:

1. An S-adenosyl-L-methionine-containing dry yeast composition, comprising:
   dry yeast comprising S-adenosyl-L-methionine; and
   4.5 to 32% by mass, based on the S-adenosyl-L-methionine-containing dry yeast composition, of a thickener,
   wherein the thickener is at least one selected from the group consisting of xanthan gum, gellan gum, and guar gum, and
   the S-adenosyl-L-methionine is accumulated in the dry yeast.

2. The composition according to claim 1, wherein the dry yeast is a yeast belonging to genus Saccharomyces.

3. The composition according to claim 2, wherein the yeast belonging to genus Saccharomyces is Saccharomyces cerevisiae.

4. A method of producing an S-adenosyl-L-methionine-containing dry yeast composition, the method comprising:
   accumulating S-adenosyl-L-methionine in an S-adenosyl-L-methionine-producing yeast;
   adding 4.5 to 32% by mass, based on the S-adenosyl-L-methionine-containing dry yeast composition, of a thickener to a yeast cell concentrate obtained from a culture solution of the S-adenosyl-L-methionine-producing yeast; and
   drying the resultant mixture,
   wherein the thickener is at least one selected from the group consisting of xanthan gum, gellan gum, and guar gum.

5. The composition according to claim 1, wherein the thickener consists of xanthan gum.

6. The composition according to claim 1, wherein the thickener consists of gellan gum.

7. The composition according to claim 1, wherein the thickener consists of guar gum.

8. The composition according to claim 1, wherein the thickener comprises xanthan gum.

9. The composition according to claim 1, wherein the thickener comprises gellan gum.

10. The composition according to claim 1, wherein the thickener comprises guar gum.

11. The composition according to claim 1, wherein the composition provides a SAMe residual rate of 99.0% to 99.8% in a stability test at 40° C. and 75% relative humidity for 60 days.

12. The method according to claim 4, wherein the composition produced provides a SAMe residual rate of 99.0% to 99.8% in a stability test at 40° C. and 75% relative humidity for 60 days.

13. The composition according to claim 1, wherein the S-adenosyl-L-methionine-containing dry yeast composition comprises 4.5% by mass or more and less than 32% by mass, based on the S-adenosyl-L-methionine-containing dry yeast composition, of the thickener.

14. The composition according to claim 1, wherein the S-adenosyl-L-methionine-containing dry yeast composition comprises 4.5 to 4.6% by mass, based on the S-adenosyl-L-methionine-containing dry yeast composition, of the thickener.

15. The composition according to claim 1, wherein the S-adenosyl-L-methionine-containing dry yeast composition consists essentially of
   dry yeast comprising S-adenosyl-L-methionine, and
   4.5 to 32% by mass, based on the S-adenosyl-L-methionine-containing dry yeast composition, of a thickener,
   wherein the thickener is at least one selected from the group consisting of xanthan gum, gellan gum, and guar gum.

16. The composition according to claim 15, wherein the S-adenosyl-L-methionine-containing dry yeast composition comprises 4.5% by mass or more and less than 32% by mass, based on the S-adenosyl-L-methionine-containing dry yeast composition, of the thickener.

17. The composition according to claim 15, wherein the S-adenosyl-L-methionine-containing dry yeast composition comprises 4.5 to 4.6% by mass, based on the S-adenosyl-L-methionine-containing dry yeast composition, of the thickener.

18. The method according to claim 4, wherein 4.5% by mass or more and less than 32% by mass, based on the S-adenosyl-L-methionine-containing dry yeast composition, of the thickener, is added to the yeast cell concentrate.

19. The method according to claim 4, wherein 4.5 to 4.6% by mass, based on the S-adenosyl-L-methionine-containing dry yeast composition, of the thickener, is added to the yeast cell concentrate.

* * * * *